United States Patent [19]

Doyle et al.

[11] Patent Number: 4,551,490
[45] Date of Patent: Nov. 5, 1985

[54] ADHESIVE COMPOSITION RESISTANT TO BIOLOGICAL FLUIDS

[75] Inventors: Arthur Doyle, Wayne; Frank M. Freeman, Lawrenceville, both of N.J.

[73] Assignee: E. R. Squibb & Sons, Inc., Princeton, N.J.

[21] Appl. No.: 567,012

[22] Filed: Dec. 30, 1983

Related U.S. Application Data

[63] Continuation-in-part of Ser. No. 507,657, Jun. 27, 1983, abandoned.

[51] Int. Cl.⁴ .............. C08L 1/26; C08L 3/04; C08L 5/02; C08L 5/06
[52] U.S. Cl. ........................ 524/22; 524/27; 524/45; 524/54; 524/55; 524/71; 524/274; 524/419; 523/111; 523/118; 428/355; 604/344
[58] Field of Search ............ 523/111, 118; 524/22, 524/27, 45, 54, 55, 71, 419, 420, 274; 424/168; 428/355, 356, 478.2; 604/338, 344

[56] References Cited

U.S. PATENT DOCUMENTS

| | | | |
|---|---|---|---|
| Re. 29,319 | 7/1977 | Nordby et al. | 128/275 |
| 3,239,478 | 3/1966 | Harlan | 428/349 |
| 3,339,546 | 9/1967 | Chen | 128/156 |
| 3,568,675 | 3/1971 | Harvey | 128/275 |
| 3,612,053 | 10/1971 | Pratt | 128/283 |
| 3,660,323 | 5/1972 | Raguse | 428/261 |
| 3,676,387 | 6/1972 | Lindlof | 524/489 |
| 3,716,503 | 2/1973 | Johnston | 523/111 |
| 3,835,857 | 9/1974 | Rogers et al. | 128/295 |
| 3,863,638 | 2/1975 | Rogers et al. | 128/295 |
| 3,908,658 | 9/1975 | Marsan | 128/283 |
| 3,972,328 | 8/1976 | Chen | 128/156 |
| 4,062,361 | 12/1977 | Poulsen | 128/283 |
| 4,123,409 | 10/1978 | Kaelble | 523/111 |
| 4,147,831 | 4/1979 | Balinth | 428/356 |
| 4,166,051 | 8/1979 | Cilento et al. | 128/283 |
| 4,181,635 | 1/1980 | Takamatsu et al. | 524/499 |
| 4,192,785 | 3/1980 | Chen et al. | 128/283 |
| 4,198,979 | 4/1980 | Cooney et al. | 128/295 |
| 4,204,540 | 5/1980 | Cilento et al. | 604/336 |
| 4,231,369 | 11/1980 | Sorensen et al. | 128/283 |
| 4,367,732 | 1/1983 | Poulsen et al. | 128/156 |
| 4,378,018 | 3/1983 | Alexander et al. | 128/295 |
| 4,393,080 | 6/1983 | Pawelchak et al. | 428/355 |
| 4,393,150 | 6/1983 | Kresner | 523/111 |

FOREIGN PATENT DOCUMENTS 1571657  7/1980  United Kingdom .

Primary Examiner—John Kight
Assistant Examiner—Nathan M. Nutter
Attorney, Agent, or Firm—Lawrence S. Levinson; Stephen B. Davis

[57] ABSTRACT

Medical grade pressure sensitive adhesive compositions comprising a homogeneous mixture of one or more polyisobutylenes or blends of one or more polyisobutylenes and butyl rubber, one or more styrene radial or block type copolymers, mineral oil, one or more water soluble hydrocolloid gums, and a tackifier. One or more water swellable cohesive strengthening agents, an antioxidant, and various other optional ingredients may be included within the adhesive composition.

25 Claims, No Drawings

ADHESIVE COMPOSITION RESISTANT TO BIOLOGICAL FLUIDS

This application is a continuation-in-part of U.S. Ser. No. 507,657 filed June 27, 1983, now abandoned.

BACKGROUND OF THE INVENTION

Various adhesive compositions suitable for medical use and in particular adapted to be used with ostomy and incontinent appliances have been disclosed in the patent literature.

Chen in U.S. Pat. No. 3,339,545 discloses an adhesive composition comprising a blend of one or more water soluble or water swellable hydrocolloids and a viscous substance such as polyisobutylene. The adhesive mass has a film of water insoluble material affixed to one surface. Such a bandage is commercially available under the trademark Stomahesive from E. R. Squibb & Sons, Inc. and is employed as a skin barrier by ostomates.

Chen et al. in U.S. Pat. No. 4,192,785 describe an adhesive composition suitable for use with an ostomy appliance consisting of a mixture of one or more hydrocolloid gums, a pressure sensitive adhesive such as one or more polyisobutylenes, and a cohesive strengthening agent. The cohesive strengthening agent can be a natural or synthetic fibrous material, finely divided cellulose, crosslinked dextran, cross-linked carboxymethylcellulose, or a starch-acrylonitrile graft copolymer.

Cilento et al. in U.S. Pat. No. 4,166,051 discloses a putty-like composition for use around a stoma consisting of a homogeneous mixture of a pressure sensitive adhesive component such as polyisobutylene, mineral oil, and hydrocolloid gums or cohesive strengthening agents or mixtures thereof.

Pawelchak et al. in U.S. Pat. No. 4,393,080 disclose adhesive compositions for medical use comprising a homogeneous mixture of polyisobutylenes and one or more natural of synthetic polymers capable of developing elastomeric properties when hydrated such as gluten and long chain polymers of methyl vinyl ether/maleic acid. The composition may also include one or more water soluble hydrocolloid gums and may additionally contain one or more water swellable cohesive strengthening agents. Additionally, one or more thermoplastic elastomers such as styrene copolymers and small amounts of mineral oil may be included within the composition.

Pratt in U.S. Pat. No. 3,612,053 discloses an ostomy sealing washer containing styrene isoprene and styrene butadiene block copolymers. Marsan in U.S. Pat. No. 3,908,658 discloses a sealing ring consisting of a mixture of mineral oil, styreneisobutylene copolymer and ethylene-vinyl acetate copolymer.

Sorensen et al. in U.S. Pat. No. 4,231,369 disclose an ostomy skin barrier consisting of a styrene copolymer having dispersed therein a water soluble hydrocolloid gum and a tackifier. Poulsen et al. in U.S. Pat. No. 4,367,732 disclose an ostomy skin barrier consisting of a water soluble hydrocolloid dispersed in a continuous phase consisting of a styrene copolymer, a hydrocarbon tackifier, a plasticizer, an antioxidant, and optionally an oily extender.

Alexander et al. in U.S. Pat. No. 4,378,018 disclose an adhesive composition for use with a male incontinence device comprising an mixture of hydrocolloid, polyhydroxy alcohol, fumed silica, and polyacrylamide.

Kresner in U.S. Pat. No. 4,393,150 discloses an adhesive bandage composition wherein the adhesive is a blend of polyisobutylene, polybutene, butyl rubber, reinforcing fiber, filler material and zinc oxide blended under heat and rolled into a thin sheet.

SUMMARY OF THE INVENTION

This invention is directed to pressure sensitive adhesive compositions particularly adapted for use in the fields of incontinence, ostomy care and wound and burn dressings.

The adhesive compositions are a homogeneous blend of mineral oil, one or more polyisobutylenes or mixtures of one or more polyisobutylenes and an elastomer such as butyl rubber, stryene radial or block type copolymers, water soluble hydrocolloid gums, water swellable cohesive strengthening agents, tackifiers, and small amounts of various other optional ingredients. By selection of specific ranges of the amounts of the above listed components, adhesive compositions are prepared having resistance to biological fluids such as urine as well as the properties of improved adhesion to the skin and stretchability.

DETAILED DESCRIPTION OF THE INVENTION

This invention is directed to pressure sensitive adhesive compositions suitable for various medical applications and, in particular suited for use in the fields of incontinence, wound drainage, wound and burn dressings and ostomy care. The adhesive compositions of this invention are resistant to erosion by moisture and biological fluids such as urine and fluids that are excreted from a stoma and can leak from a collection appliance. Also, the adhesive compositions of this invention are non-irritating to the human skin.

Thus, the pressure sensitive adhesive compositions of this invention can be prepared in the form of adhesive strips to hold an external type male incontinence device in place or to attach a female incontinence or wound drainage device to the body of the user. The adhesive compositions of this invention can also be prepared as a skin barrier or the adhesive faceplate of a drainable ostomy pouch and is particularly suitable for use by those ostomates who have a urinary diversion stoma. The adhesive compositions of this invention can also be employed in multilayered occlusive dressings such as those described by Pawelchak et al. in U.S. Ser. No. 370,893 filed April 22, 1982, now abandoned in favor of U.S. Ser. No. 705,859. Such dressings are useful in treating skin lesions such as dermal ulcers and pressure sores as well as in burn therapy.

The pressure sensitive adhesive compositions of this invention are a homogeneous blend of mineral oil, one or more polyisobutylenes or mixture of one or more polyisobutylenes and an elastomer such as butyl rubber, styrene radial or block type copolymers, water soluble hydrocolloid gums, water swellable cohesive strengthening agents, and a tackifier. In addition, small amounts of various other optional ingredients can be included. By employing these ingredients in certain specific amounts, compositions are obtained having the desired balance of the properties of adhesion, durability and stretchability.

The polyisobutylene component of the pressure sensitive adhesive composition functions to provide adhesion to dry body surfaces, i.e., dry tack, and holds the entire composition together. Preferably, the polyisobutylenes employed are one or more low molecular weight polyisobutylenes having a viscosity average molecular weight of from about 36,000 to about 58,000 (Florey). Such polyisobutylenes are commercially available under the trademark Vistanex from Exxon as grades LM-MS and LM-MH. Optionally, in order to increase the elasticity, tear resistance, and cohesiveness of the adhesive compositions as indicated by a reduction in the cold flow of the adhesive composition, an elastomeric polymer such as butyl rubber can be blended with the polyisobutylenes. Butyl rubber is a copolymer of isobutylene with a minor amount of isoprene having a viscosity average molecular weight of from about 350,000 to about 450,000 (Florey). The polyisobutylenes and butyl rubber can be blended together on a weight basis of from about 4 parts polyisobutylene to about 1 part butyl rubber to about 1 part polyisobutylene to about 4 parts butyl rubber with about 1 part low molecular weight polyisobutylene to about 2 parts butyl rubber being preferred.

The styrene radial or block copolymer component of the pressure sensitive composition functions to provide extensibility and both rapid and complete recovery from modular strains to the composition. Particularly suitable styrene copolymers include styrene-butadiene-styrene (S-B-S) and styrene-isoprene-styrene (S-I-S) block type copolymers both of which are commercially available, for example, from Shell Chemical Co. under the tradename Kraton as Kraton 1100, 1101, 1102, 1107, etc. Preferably, one or more styrene-isoprene-styrene (S-I-S) block type copolymers are employed.

The pressure sensitive adhesive compositions of this invention contain from about 5% to about 30% by weight of polyisobutylenes or blends of polyisobutylenes and an elastomer such as butyl rubber and from about 3% to about 20% by weight of styrene copolymers.

Mineral oil is included within the pressure sensitive adhesive composition to increase the aggressiveness of the bonding without requiring undue pressure in applying the adhesive composition to the body, i.e., "wet grab". The mineral oil also functions to increase the stretchability of the final composition. The mineral oil is present in the adhesive compositions of this at from about 8% to about 40% by weight of the final composition.

One or more water soluble hydrocolloid gums are also included within the pressure sensitive compositions. The water soluble hydrocolloids enable the adhesive compositions to adhere to moist body surfaces, i.e., wet tack. Optionally, one or more water swellable cohesive strengthening agents may also be included within the pressure sensitive adhesive compositions. The cohesive strengthening agents along with the water soluble hydrocolloid gums function to control the rate of hydration of the adhesive compositions and enable them to resist erosion by biological fluids such as urine. Suitable water soluble hydrocolloid gums include sodium carboxymethylcellulose, which is preferred, pectin, gelatin, guar gum, locut bean gum, gum karaya, and mixtures thereof. Suitable water swellable cohesive strengthening agents include finely divided substantially water insoluble cross-linked sodium carboxymethylcellulose such as that commercially available under the trademark AcDiSol or Aqualon and available commercially from Hercules Corp. or FMC or that described in U.S. Pat. No. 3,589,364, finely divided substantially water insoluble starch-acrylonitrile graft copolymer such as that described in U.S. Pat. No. 3,661,815 and commercially available from the Grain Processing Corp., and finely divided substantially water insoluble cross-linked dextran such as that commercially available under the trademark Sephadex. The preferred water swellable cohesive strengthening agent is cross-linked sodium carboxymethylcellulose.

The water soluble hydrocolloid gums are present at from about 15% to about 65% by weight of the adhesive compositions and the water swellable cohesive strengthening agents are present at up to about 15% by weight of the adhesive compositions provided that the water soluble hydrocolloid gums and cohesive strengthening agents together are present at from about 15% to about 65% by weight of the adhesive compositions.

The pressure sensitive adhesive compositions of this invention also include from about 7.5% to about 15% by weight of a tackifier. Suitable tackifiers include the pentaerythritol esters of rosin commercially available from Hercules under the trademark Pentalyn H, trimethylol propane ester of rosin commercially available from Hercules under the tradename Staybelite Ester 10, and the beta pinine resins such as Piccolyte S115 or the cyclopentadiene resins commercially available from Exxon such as Escorez 5300 or the Arakawa cyclic tackifiers namely the Arkon products.

Small amounts, i.e., less than about 5% by weight of the adhesive composition, of other optional ingredients may be included in the adhesive composition. For example, up to about 0.5% by weight of an antioxidant such as zinc dibutyldithiocarbamate (commercially available from R. T. Vanderbilt Co. under the tradename Butyl Zimate) or those available from Ciba Geigy such as Irganox 1010, tetrakis [methylene(3,5-ditert-butyl-4-hydroxyhydrocinnamate)methane], or Irganox 1076, octadecyl 3-[3,5-ditert-butyl-4'-hydroxy-phenyl]-propionate, a deodorant such as chlorophyllins, or a perfume agent may be included. In addition, small amounts of a pharmacologically active ingredient can be included in the adhesive composition. For example, an antibiotic or antimicrobial agent such as neomycin, an antiseptic agent such as povidone iodine, an antiinflammatory agent such as hydrocortisone or triamcinolone acetonide, or a skin protective agent such as zinc oxide. When the bandage is used as a burn dressing, small amounts of active ingredients such as silver sulfadiazine, sulfadiazine, and other silver compounds can be included in the composition. Also, small amounts, i.e., less than 1% by weight of the adhesive composition, of physical reinforcing agents that form Van der Walls bonds with the polymeric substituents can be included such as carbon black, polyaramids (commercially available under the tradename Kevlar), hydrated silicas, etc.

The adhesive compositions of this invention are prepared by combining the polyisobutylenes, optional butyl rubber, styrene copolymers, mineral oil, and antioxidant with heating and agitation in a heavy duty high shear sigma blade or equivalent type mixer. The mixture is heated from about 120° to about 150° C. with temperatures of 135° C. required when butyl rubber is present in the composition and mixing is continued until the mass is homogeneous. The mixture is then cooled and the tackifier is added with mixing at about 100° C. The water soluble gums, water swellable cohesive strengthening agents, mineral oil, and the other optional ingredients are added with continued heating and mixing at about 80° to 90° C. The resultant homogeneous mass is then extruded and rolled or pressed to desired thickness.

By further adjusting the percentage of the components of the adhesive compositions of this invention, properties such as duration of adhesion, resistance to erosion, stretchability, and removal without skin stripping can be varied according to the particular use. Thus, if the adhesive composition is to be used as an ostomy skin barrier, the properties of duration of adhesive and resistance to erosion are most important. If the adhesive composition is to be used with a male incontinence device, stretchability and resistance to erosion are most important whereas avoiding stripping of the skin becomes important for wound and burn dressings.

Adhesive compositions of the present invention preferred for use as ostomy adhesives include from about 20% to about 30% by weight one or more low molecular weight polyisobutylenes or a blend of one or more low molecular weight polyisobutylenes and butyl rubber, from about 3% to about 10% by weight of one or more styrene-isoprene-styrene block type copolymers, from about 9% to about 25% by weight of mineral oil, from about 30% to about 65% by weight of one or more water soluble hydrocolloid gums, up to about 15% by weight of one or more water swellable cohesive strengthening agents provided that the water soluble hydrocolloid gums and cohesive strengthening agents together are present at from about 30% to about 65% by weight of said composition, preferably from about 35% to about 55% by weight of said composition, and from about 7.5% to about 15% by weight of a tackifier.

Adhesive compositions of the present invention preferred for use in affixing a male incontinence device include from about 5% to about 15% by weight of one or more low molecular weight polyisobutylenes or a blend of one or more low molecular weight polyisobutylenes and butyl rubber, from about 10% to about 20% by weight of one or more styrene-isoprene-styrene block type copolymers, from about 20% to about 40% by weight of mineral oil, from about 25% to about 65% by weight of one or more water soluble hydrocolloid gums, up to about 15% by weight of one or more water swellable cohesive strengthening agents provided that the water soluble hydrocolloid gums and cohesive strengthening agents together are present at from about 25% to about 65% by weight of said composition, most preferably from about 25% to 50% by weight of said composition, and from about 7.5% to about 15% by weight of a tackifier.

Adhesive compositions of the present invention preferred for use in a wound or burn dressing include from about 5% to about 15% by weight of one or more low molecular weight polyisobutylenes or a blend of one or more low molecular weight polyisobutylenes and butyl rubber, from about 10% to about 20% by weight of one or more styrene-isoprene-styrene block type copolymers, from about 20% to about 40% by weight of mineral oil, from about 30% to about 60% by weight of one or more water soluble hydrocolloid gums, up to about 15% by weight of one or more water swellable cohesive strengthening agents provided that the water soluble hydrocolloid gums and cohesive strengthening agents together are present at from about 30% to about 65% by weight of said composition, and from about 7.5% to about 10% by weight of a tackifier.

The adhesive compositions of this invention may be packaged in strip form and employed to hold a male incontinence device in place as described by Rodgers et al. in U.S. Pat. Nos. 3,835,857 and 3,863,638. The adhesive compositions may also be employed to affix various medical devices to the body such as a female incontinence device as described by Cooney et al. in U.S. Pat. No. 4,198,979, a wound drainage system as described by Harvey in U.S. Pat. No. 3,568,675 and by Nordby in U.S. Pat. No. 3,954,105, a catheter, or an electronic probe.

If desired, the adhesive compositions may be in a wafer shape with a thin film of polymeric material laminated to one side so that they can be employed as skin barriers by ostomates. In addition, a coupling element could be attached to the polymeric surface of the skin barrier as taught by Steer et al. in British Pat. No. 1,571,657.

The adhesive compositions may be employed as the mounting faceplate of a conventional ostomy pouch and, in particular, a drainable type pouch intended to remain on the body for several days.

The adhesive compositions of this invention may be sterilized by means of gamma radiation.

The following examples are illustrative of the invention. Other suitable adhesive compositions can be obtained by minor variations in the amounts of ingredients employed.

EXAMPLE 1

This example is directed to preparing an adhesive mass having the following composition:

|  | Percent by weight |
| --- | --- |
| Polyisobutylene (Vistanex LM-MH) | 10.2 |
| Styrene-isoprene-styrene copolymer (Kraton 1107) | 12.6 |
| Mineral oil | 25.1 |
| Zinc dibutyldithiocarbamate (Butyl Zimate) | 0.06 |
| Tackifier (Pentalyn H) | 8.94 |
| Sodium carboxymethylcellulose | 31.0 |
| Cross-linked sodium carboxymethylcellulose (Ac-Di-Sol) | 12.1 |

The mineral oil (185.7 g.), polyisobutylene (75.8 g.), Kraton 1107 (92.8 g.), and Butyl Zimate (0.4 g.) are combined in a sigma blade mixer with heating (about 115° C.) and agitating for approximately 1.0 to 2.5 hours. The mixture is cooled to about 100° C. and after another 30 minutes of blending, the sodium carboxymethylcellulose (229.2 g.), cross-linked sodium carboxymethylcellulose (89.1 g.) and Pentalyn H (66.1 g.) are added. Mixing is continued at about 100° C. for 30 minutes until a homogeneous mass is obtained.

This mass is allowed to cool and it is flattened to the desired thickness. Silicone coated release paper is applied to both sides and it is cut into strips for use with an external catheter male incontinence device.

EXAMPLES 2-25

Following the procedure of Example 1 but employing the following ingredients on a weight percent basis other adhesive compositions within the scope of the invention are prepared.

| Ingredient | 2 | 3 | 4 | 5 | 6 | 7 | 8 | 9 | 10 | 11 | 12 | 13 |
|---|---|---|---|---|---|---|---|---|---|---|---|---|
| Polyisobutylene (Vistanex LM-MH) | 11.68 | 11.68 | 7.75 | 5.9 | 6.7 | — | 10 | 15 | 13 | — | 15 | 15 |
| Polyisobutylene (Vistanex LM-MS) | — | — | — | — | — | 10.8 | — | — | — | 15 | — | — |
| Guar Gum | — | — | — | — | — | 26.0 | — | — | — | — | — | — |
| Locust Bean Gum | — | — | — | — | — | — | — | 20 | — | — | — | — |
| Pectin | — | — | — | — | — | — | 10 | — | 10 | — | — | — |
| Karaya | — | — | — | — | — | — | — | — | — | 15 | — | — |
| Gelatin | — | — | — | — | — | — | 10 | — | — | — | — | — |
| Sodium carboxymethylcellulose | 31.74 | 28.24 | 25.1 | 26.3 | 21.9 | — | 11 | — | 17 | 15 | 20 | 20 |
| Cross-linked sodium Carboxymethylcellulose | 12.34 | 12.34 | 9.1 | 10.5 | 8.0 | — | — | 12 | 12 | 8 | 12 | — |
| Starch-acrylonitrile graft copolymer (Grain Processing Corp. Polymer 35-A-100) | — | — | — | — | — | 12.0 | — | — | — | — | — | 10 |
| Cross-linked dextran (Sephadex CM-C50) | — | — | — | — | — | — | 10 | — | — | — | — | — |
| Mineral Oil | 23.4 | 26.86 | 30.4 | 31.5 | 40.5 | 28.5 | 20 | 30 | 25 | 24 | 27 | 35 |
| S—I—S copolymer (Kraton 1107) | 11.68 | 11.68 | 19.2 | 16.7 | 13.2 | 15.0 | 20 | — | 15 | — | 18 | 12 |
| S—B—S copolymer (Kraton 1102) | — | — | — | — | — | — | — | 15 | — | 13 | — | — |
| Tackifier (Pentalyn H) | 9.10 | 9.14 | 12.3 | 8.9 | 9.6 | 7.5 | 8.99 | 7.98 | 7.98 | 9.99 | 7.98 | 7.98 |
| Antioxidant | 0.06 | 0.06 | 0.15 | 0.2 | 0.1 | 0.2 | 0.01 | 0.02 | 0.02 | 0.01 | 0.02 | 0.02 |
| Butyl rubber (Grade 065) | — | — | — | — | — | — | — | — | — | — | — | — |

| Ingredient | 14 | 15 | 16 | 17 | 18 | 19 | 20 | 21 | 22 | 23 | 24 | 25 |
|---|---|---|---|---|---|---|---|---|---|---|---|---|
| Polyisobutylene (Vistanex LM-MH) | 15 | — | 7.3 | 24.75 | 8.0 | 8.0 | — | 10.0 | 20.0 | 20.5 | 8.0 | 8.0 |
| Polyisobutylene (Vistanex LM-MS) | — | 15 | 7.3 | — | — | — | 10.0 | — | — | — | — | — |
| Guar Gum | — | 10 | — | — | — | — | 30.0 | — | 20.0 | — | — | — |
| Locust Bean Gum | — | — | — | — | — | — | — | — | — | — | — | — |
| Pectin | 10 | — | — | 15.0 | 15.0 | 14.33 | — | — | — | 19.66 | 15.0 | 16.0 |
| Karaya | — | — | — | — | — | — | — | — | — | — | — | — |
| Gelatin | — | — | — | 15.0 | 15.0 | 14.33 | — | — | — | 19.67 | 15.0 | 16.0 |
| Sodium carboxymethylcellulose | 15 | 30 | 36 | 15.0 | 15.0 | 14.34 | — | 37.5 | 15.0 | 19.67 | 15.0 | 16.0 |
| Cross-linked sodium Carboxymethylcellulose | 10 | 10 | 12.3 | — | — | — | 15.0 | 10.0 | — | — | — | — |
| Starch-acrylonitrile graft copolymer (Grain Processing Corp. Polymer 35-A-100) | — | — | — | — | — | — | — | — | — | — | — | — |
| Cross-linked dextran (Sephadex CM-C50) | — | — | — | — | — | — | — | — | — | — | — | — |
| Mineral Oil | 30 | 15 | 17.59 | 13.5 | 13.5 | 13.5 | 16.0 | 9.0 | 20.0 | 10.0 | 13.5 | 9.75 |
| S—I—S copolymer (Kraton 1107) | — | 12 | 10.25 | 6.75 | 6.75 | 6.75 | 5.0 | 3.0 | 10.0 | 3.0 | — | 10.0 |
| S—B—S copolymer (Kraton 1102) | 11 | — | — | — | — | — | — | — | — | — | 6.75 | — |
| Tackifier (Pentalyn H) | 8.99 | 7.99 | 9.2 | 10.0 | 10.0 | 12.0 | 8.0 | 10.0 | 15.0 | 7.5 | 10.0 | 7.5 |
| Antioxidant | 0.01 | 0.01 | 0.06 | — | 0.50 | 0.50 | 0.8 | 0.5 | — | — | 0.50 | 0.50 |
| Butyl rubber (Grade 065) | — | — | — | — | 16.25 | 16.25 | 15.5 | 20.0 | — | — | 16.25 | 16.25 |

What is claimed is:

1. A pressure sensitive adhesive composition suitable for medical purposes consisting essentially of a substantially homogeneous mixture on a percent weight basis of from about 5% to about 30% by weight of one or more polyisobutylenes or a blend of one or more polyisobutylenes and butyl rubber, from about 3.0% to about 20% by weight of one or more styrene radial or block type copolymers, from about 8.0% to about 40% by weight of mineral oil, from about 15% to about 65% by weight of one or more water soluble hydrocolloid gums, up to about 15% by weight of one or more water swellable cohesive strengthening agents provided that said water soluble hydrocolloid gums and said water swellable cohesive strengthening agents together are present at from about 15% to about 65% by weight of said composition, and from about 7.5% to about 15% by weight of a tackifier.

2. An adhesive composition of claim 1 wherein said water soluble hydrocolloid is selected from the group consisting of sodium carboxymethylcellulose, pectin, gelatin, guar gum, locust bean gum, gum karaya, and mixtures thereof and said water swellable cohesive strengthening agent is selected from the group consisting of cross-linked sodium carboxymethylcellulose, starch-acrylonitrile graft copolymers, and cross-linked dextran.

3. An adhesive composition of claim 2 wherein said styrene copolymer is a styrene-isoprene-styrene or a styrene-butadiene-styrene block polymer.

4. An adhesive composition of claim 3 wherein said styrene copolymer is a styrene-isoprene-styrene block copolymer.

5. An adhesive composition of claim 4 wherein said polyisobutylenes are one or more low molecular weight polyisobutylenes.

6. A pressure sensitive adhesive composition particularly suited for use in attaching a male incontinence device to a patient consisting essentially of a substantially homogeneous mixture on a percent weight basis of from about 5% to about 15% by weight of one or more low molecular weight polyisobutylenes or a blend of one or more low molecular weight polyisobutylenes and butyl rubber, from about 10% to about 20% by weight of a styrene block type copolymer selected from the group consisting of styrene-isoprene-styrene and styrene-butadiene-styrene block copolymers, from about 20% to about 40% by weight of mineral oil, from about 25% to about 65% by weight of a water soluble hydrocolloid selected from the group consisting of sodium carboxymethylcellulose, pectin, gelatin, guar gum, locust bean gum, gum karaya, and mixtures thereof, up to about 15% by weight of a water swellable cohesive strengthening agent selected from the group consisting of cross-linked sodium carboxymethylcellulose, starch-acrylonitrile graft copolymer, and cross-linked dextran provided that said water soluble hydrocolloids and said water swellable cohesive strengthening agents are together present at from about 25% to about 65% by weight of said composition, from about 7.5% to about 15% by weight of a tackifier, and up to about 0.5% by weight of an antioxidant.

7. An adhesive composition of claim 6 wherein said styrene copolymer is a stryene-isoprene-styrene block copolymer.

8. An adhesive composition of claim 7 wherein said water soluble hydrocolloid and said water swellable cohesive strengthening agent together are present at from about 25% to about 50% by weight of said adhesive composition.

9. An adhesive composition of claim 8 wherein said water soluble hydrocolloid is sodium carboxymethylcellulose and said water swellable cohesive strengthening agent is cross-linked sodium carboxymethylcellulose.

10. An adhesive composition of claim 6 wherein said tackifier is a pentaerythritol ester of rosin.

11. An adhesive composition of claim 6 wherein said antioxidant is zinc dibutyldithiocarbamate.

12. A pressure sensitive adhesive composition particularly suited for use as an ostomy skin barrier consisting essentially of a substantially homogeneous mixture on a percent weight basis of from about 20% to about 30% by weight of one or more low molecular weight polyisobutylenes or a blend of one or more low molecular weight polyisobutylenes and butyl rubber, from about 3% to about 10% by weight of a styrene block type copolymer selected from the group consisting of styrene-isoprene-styrene and styrene-butadiene-styrene block copolymers, from about 9% to about 25% by weight of mineral oil, from about 30% to about 65% by weight of a water soluble hydrocolloid selected from the group consisting of sodium carboxymethylcellulose, pectin, gelatin, guar gum, locust bean gum, gum karaya, and mixtures thereof, up to about 15% by weight of a water swellable cohesive strengthening agent selected from the group consisting of cross-linked sodium carboxymethylcellulose, starch-acrylonitrile graft copolymer, and cross-linked dextran provided that said water soluble hydrocolloids and said water swellable cohesive strengthening agents are together present at from 30% to about 65% by weight of said composition, from about 7.5% to about 15% by weight of a tackifier, and up to about 0.5% by weight of an antioxidant.

13. An adhesive composition of claim 12 wherein said styrene copolymer is a styrene-isoprene-styrene block polymer.

14. An adhesive composition of claim 13 wherein said water soluble hydrocolloid and said water swellable cohesive strengthening agent together are present at from about 35% to about 55% by weight of said adhesive composition.

15. An adhesive composition of claim 14 wherein said water soluble hydrocolloid is a mixture of more than one of pectin, gelatin, and sodium carboxymethylcellulose.

16. An adhesive composition of claim 12 wherein said tackifier is a pentaerythritol ester of rosin.

17. An adhesive composition of claim 12 wherein said antioxidant is zinc dibutyldithiocarbamate.

18. A pressure sensitive adhesive composition particularly suited for use in a wound or burn dressing consisting essentially of a substantially homogeneous mixture on a percent weight basis of from about 5% to about 15% by weight of one or more low molecular weight polyisobutylenes or a blend of one or more low molecular weight polyisobutylenes and butyl rubber, from about 10% to about 20% by weight of a styrene block copolymer selected from the group consisting of styrene-isoprene-styrene and styrene-butadiene-styrene block copolymers, from about 20% to about 40% by weight of mineral oil, from about 30% to about 60% by weight of a water soluble hydrocolloid selected from the group consisting of sodium carboxymethylcellulose, pectin, gelatin, guar gum, locust bean gum, gum karaya, and mixture thereof, up to about 15% by weight of a water swellable cohesive strengthening agent selected from the group consisting of cross-linked sodium carboxymethylcellulose, starch-acrylonitrile graft copolymer, and cross-linked dextran provided that said water soluble hydrocolloids and said water swellable cohesive strengthening agents are together present at from about 30% to about 65% by weight of said composition, from about 7.5% to about 10% by weight of a tackifier, and up to about 0.5% of an antioxidant.

19. An adhesive composition of claim 18 wherein said styrene copolymer is a styrene-isoprene-styrene block copolymer.

20. An adhesive composition of claim 18 wherein said tackifier is a pentaerythritol ester of rosin.

21. An adhesive composition of claim 18 wherein said antioxidant is zinc dibutyldithiocarbamate.

22. A pressure sensitive adhesive composition particularly suited for use as an ostomy skin barrier consisting essentially of a substantially homogeneous mixture on a percent weight basis of from about 5% to about 30% by weight of a blend of one or more low molecular weight polyisobutylenes and butyl rubber, said polyisobutylenes and butyl rubber blended together on a weight basis of from about 4 parts polyisobutylene to about 1 part butyl rubber to about 1 part polyisobutylene to about 4 parts butyl rubber, from about 3% to about 10% by weight of a styrene-isoprene-styrene block copolymer, from about 9% to about 25% by weight of mineral oil, from about 35% to about 55% by weight of a mixture of more than one of pectin, gelatin, and sodium carboxymethylcellulose, from about 7.5% to about 15% by weight of a tackifier, and up to about 0.5% by weight of an antioxidant.

23. An adhesive composition of claim 22 wherein said low molecular weight polyisobutylene and said butyl rubber are blended on a weight basis of from about 1 part low molecular weight polyisobutylene to about 2 parts butyl rubber.

24. An adhesive composition of claim 23 wherein said tackifier is a pentaerythritol ester of rosin.

25. An adhesive composition of claim 23 wherein said antioxidant is zinc dibutyldithiocarbamate.

* * * * *